United States Patent
Tribbett

(10) Patent No.: US 10,667,595 B2
(45) Date of Patent: Jun. 2, 2020

(54) MODULAR COSMETIC SYSTEM AND METHOD OF USE

(71) Applicant: Heather J. Tribbett, Loveland, CO (US)

(72) Inventor: Heather J. Tribbett, Loveland, CO (US)

(*) Notice: Subject to any disclaimer, the term of this patent is extended or adjusted under 35 U.S.C. 154(b) by 602 days.

(21) Appl. No.: 15/376,201

(22) Filed: Dec. 12, 2016

(65) Prior Publication Data

US 2017/0164717 A1    Jun. 15, 2017

Related U.S. Application Data

(60) Provisional application No. 62/266,140, filed on Dec. 11, 2015.

(51) Int. Cl.

| | |
|---|---|
| *A45D 24/00* | (2006.01) |
| *A45D 40/24* | (2006.01) |
| *A61K 8/02* | (2006.01) |
| *A61Q 1/02* | (2006.01) |
| *A61Q 1/10* | (2006.01) |
| *A61K 8/88* | (2006.01) |
| *A61K 8/19* | (2006.01) |
| *A61K 8/97* | (2017.01) |
| *A61K 8/26* | (2006.01) |
| *A61K 8/36* | (2006.01) |
| *A61K 8/25* | (2006.01) |
| *A61K 8/27* | (2006.01) |
| *A61K 8/60* | (2006.01) |
| *A61K 8/92* | (2006.01) |

(Continued)

(52) U.S. Cl.
CPC .............. *A45D 40/24* (2013.01); *A45D 33/00* (2013.01); *A45D 44/005* (2013.01); *A61K 8/022* (2013.01); *A61K 8/19* (2013.01); *A61K 8/25* (2013.01); *A61K 8/26* (2013.01); *A61K 8/27* (2013.01); *A61K 8/34* (2013.01); *A61K 8/361* (2013.01); *A61K 8/375* (2013.01); *A61K 8/602* (2013.01); *A61K 8/88* (2013.01); *A61K 8/922* (2013.01); *A61K 8/927* (2013.01); *A61K 8/97* (2013.01); *A61Q 1/02* (2013.01); *A61Q 1/10* (2013.01); *A45D 2200/058* (2013.01); *A45D 2200/25* (2013.01); *A61K 2800/882* (2013.01); *A61Q 1/12* (2013.01)

(58) Field of Classification Search
CPC ...... A45D 40/24; A45D 2200/25; A61Q 1/02; A61Q 1/10; A61K 8/022; A61K 8/19; A61K 8/25; A61K 8/26; A61K 8/27; A61K 8/361; A61K 8/602; A61K 8/88; A61K 8/922; A61K 8/97
See application file for complete search history.

(56) References Cited

U.S. PATENT DOCUMENTS

| | | |
|---|---|---|
| 5,086,791 A | 2/1992 | Ferrari |
| 5,494,056 A | 2/1996 | Reynolds |

(Continued)

*Primary Examiner* — Nicholas D Lucchesi
(74) *Attorney, Agent, or Firm* — Faegre Drinker Biddle & Reath LLP

(57) ABSTRACT

A modular cosmetics system and method of use is provided. In one embodiment, a modular cosmetic system is disclosed that includes a primary and a color component. The modular cosmetic system may also include a modifier. The primary, color, and modifier component may be combinable together in multiple ways to create every kind of makeup of any color and texture of a user's choosing.

13 Claims, 8 Drawing Sheets

(51) Int. Cl.
  *A61K 8/34*   (2006.01)
  *A45D 44/00*  (2006.01)
  *A61K 8/37*   (2006.01)
  *A45D 33/00*  (2006.01)
  *A61Q 1/12*   (2006.01)

(56) References Cited

U.S. PATENT DOCUMENTS

| | | |
|---|---|---|
| 5,509,960 A * | 4/1996 | Simpson ............... B82Y 30/00 |
| | | 106/417 |
| 5,893,373 A | 4/1999 | Reynolds |
| 6,000,407 A | 12/1999 | Galazin |
| 6,058,942 A | 5/2000 | Eng |
| 6,309,627 B1 * | 10/2001 | Golz-Berner ........ A61K 8/0275 |
| | | 424/401 |
| 6,703,027 B2 * | 3/2004 | Kurosawa ............ A61K 8/025 |
| | | 424/401 |
| 6,739,345 B2 | 5/2004 | Stanley, III |
| 6,740,590 B1 * | 5/2004 | Yano ...................... C09G 1/02 |
| | | 257/E21.304 |
| 6,761,896 B1 | 7/2004 | Znaiden et al. |
| 6,857,432 B2 | 2/2005 | de Laforcade |
| 6,896,889 B2 * | 5/2005 | Chevalier ................ A61K 8/25 |
| | | 424/401 |
| 7,165,559 B1 | 1/2007 | Goodman |
| 8,464,732 B2 | 6/2013 | Wong |
| 8,603,505 B2 * | 12/2013 | Brown ................... A61K 8/042 |
| | | 424/401 |
| 8,855,974 B2 | 10/2014 | Cho et al. |
| 8,895,038 B2 | 11/2014 | Ancorotti et al. |
| 8,899,242 B2 | 12/2014 | Wong |
| 9,226,890 B1 * | 1/2016 | Lamberty ............... A61K 8/891 |
| 9,345,649 B2 * | 5/2016 | Brown ................... A61K 8/042 |
| 2002/0082745 A1 | 6/2002 | Wilmott et al. |
| 2003/0072780 A1 * | 4/2003 | Ionita-Manzatu ........ A61K 8/02 |
| | | 424/401 |
| 2003/0187518 A1 | 10/2003 | Carls |
| 2004/0120909 A1 | 6/2004 | Lee et al. |
| 2004/0137026 A1 * | 7/2004 | Golz-Berner ........ A61K 8/8123 |
| | | 424/401 |
| 2005/0163813 A1 * | 7/2005 | Kosbach ................. A61K 8/26 |
| | | 424/401 |
| 2005/0201961 A1 * | 9/2005 | Lu .......................... A61K 8/585 |
| | | 424/63 |
| 2006/0067906 A1 * | 3/2006 | Sanders ................... A61K 8/37 |
| | | 424/70.12 |
| 2006/0078527 A1 * | 4/2006 | Midha ..................... A61K 8/03 |
| | | 424/70.27 |
| 2006/0127332 A1 * | 6/2006 | Rodrigues .............. A61K 8/375 |
| | | 424/63 |
| 2008/0152680 A1 * | 6/2008 | Brown ................... A61K 8/042 |
| | | 424/401 |
| 2009/0117060 A1 | 5/2009 | Golz-Berner et al. |
| 2009/0232858 A1 * | 9/2009 | Peppas ................... A61K 9/0004 |
| | | 424/401 |
| 2010/0024836 A1 | 2/2010 | Gegennes |
| 2011/0164263 A1 | 7/2011 | Samain et al. |
| 2012/0067364 A1 | 3/2012 | Wong |
| 2014/0209114 A1 | 7/2014 | Johnson |
| 2014/0305466 A1 | 10/2014 | Silva |
| 2015/0086945 A1 | 3/2015 | Yamanashi et al. |

* cited by examiner

| COLOR | MATTE and/or LUSTER | UNATTACHED |
|---|---|---|
| 0 Sparkle (1 part) | 1.5 - 2 parts | 2 + parts |
| 1 Black (1 part) | 1.5 - 2 parts | 2 + parts |
| 2N (1 part) | 1.5 - 2 parts | 2 + parts |
| 4N (1 part) | 1.5 - 2 parts | 2 + parts |
| 6N (1 part) | 1.5 - 2 parts | 2 + parts |
| 8N (1 part) | 1.5 - 2 parts | 2 + parts |
| 10N (1 part) | 1.5 - 2 parts | 2 + parts |
| 12 White (1 part) | 1.5 - 2 parts | 2 + parts |
| RED (1 part) | 1.5 - 2 parts | 2 + parts |
| YELLOW (1 part) | 1 - 1.5 parts | 1 + parts |
| BLUE (1 part) | 1 - 1.5 parts | 1 + parts |
| Bright Red (1 part) | 1.5 - 2 parts | 2 + parts |
| Bright Yellow (1 part) | 1.5 - 2 parts | 2 + parts |
| Dark Blue (1 part) | 1.5 - 2 parts | 2 + parts |
| Green (1 part) | 1.5 - 2 parts | 2 + parts |
| Purple (1 part) | 1.5 - 2 parts | 2 + parts |
| Orange (1 part) | 1.5 - 2 parts | 2 + parts |

FIG. 4

MODULAR COSMETIC SYSTEM AND METHOD OF USE

CROSS-REFERENCE TO RELATED APPLICATIONS

This application claims the benefit of U.S. Provisional Patent Application Ser. No. 62/266,140, filed Dec. 11, 2015, the entire disclosure of which is hereby incorporated by reference for all that it teaches and for all purposes.

FIELD

Embodiments of the present invention are generally related to a method and system for a customizable cosmetics or makeup line that encompasses the totality of makeup functions to provide total control over purpose, color, and texture.

BACKGROUND

From daily makeup to specialty applications, cosmetics can serve numerous functions. However, the current commercial state of the beauty industry is limited to convenience items that serve only specific purposes. Even current mix-your-own makeup lines are limited by purpose, the cause of which lies partially in the idea that "bases" determine texture, and that these "bases" are specifically formulated to color, which can vary significantly. Also, texture is often a personal preference instead of an absolute in the function of makeup.

Additionally, a problem with convenience cosmetics is the number and amount of chemicals used in the products and sensitivities to such chemicals are difficult to pinpoint because isolation of the sensitivity is difficult if not impossible. Another issue with convenience cosmetics within the cosmetic industry is the ideology that one must know the "rules" of makeup to apply or use it correctly. Arbitrary rules that change with the fads and/or the marketing ploys of cosmetic brands perpetuate such problems. These rules limit the imagination of the consumer and can harm the self-worth of an individual by defining the outcome as beautiful or ugly, a major move away from the simplest and truest purpose of makeup which is to create illusion.

By way of providing additional background, context, and to further satisfy the written description requirement of 35 U.S.C. § 112, the following documents are hereby incorporated by reference in their entirety:

U.S. Pat. Appl. Pub. No. 2002/0082745 entitled "Method and System for Producing Customized Cosmetic and Pharmaceutical Formulations on Demand";
U.S. Pat. No. 6,739,345 entitled "Make up Application Kit";
U.S. Pat. No. 8,895,038 entitled "Method for Preparing a Two-Coloured Cosmetic";
U.S. Pat. No. 7,165,559 entitled "Cosmetic Makeup Kit";
U.S. Pat. No. 8,464,732 entitled "Facial Make-up Application Machine and Make-Up Application Method Using the Same"
U.S. Pat. No. 8,855,974 entitled "System and Method for Recommending Sensitive Make-Up Based on Skin Tone or User";
U.S. Pat. No. 8,899,242 entitled "Eyes Make-Up Application Machine";
U.S. Pat. No. 5,086,791 entitled "Process for the Production of a Cosmetic Product with Powders of Several Colors or Different Characteristics";
U.S. Pat. No. 5,494,056 entitled "Method for Application of Cosmetics";
U.S. Pat. No. 5,893,373 entitled "Method for Application of Cosmetics";
U.S. Pat. No. 6,000,407 entitled "Cosmetic Personal Color Analysis Method and Kit Using Value, Scale, Colors, Seasonal Color Designation, and Charts";
U.S. Pat. No. 6,058,942 entitled "Multiple-Component Cosmetic Product and Method of Making Same";
U.S. Pat. No. 6,761,896 entitled "Skin Cosmetic Care System and Method";
U.S. Pat. No. 6,857,432 entitled "Cosmetics Product and Marketing System";
U.S. Pat. Appl. Pub. No. 2014/0305466 entitled "Cosmetic Application Tool and Container System and Method";
U.S. Pat. Appl. Pub. No. 2015/0086945 entitled "Makeup Application Assistance Device, Makeup Application Assistance System, and Makeup Application Assistance Method";
U.S. Pat. Appl. Pub. No. 2004/0120909 entitled "Cosmetic method and composition for enhancing attractiveness";
U.S. Pat. Appl. Pub. No. 2009/0117060 entitled "Cosmetic Process for the Treatment of the Skin with Sun-Protection Products and Sun-Protection Products Combination";
U.S. Pat. Appl. Pub. No. 2010/0024836 entitled "Kit for Applying a Cosmetic Composition";
U.S. Pat. Appl. Pub. No. 2011/0164263 entitled "Method of Applying Makeup and Apparatus for Implementing Such a Method";
U.S. Pat. Appl. Pub. No. 2012/0067364 entitled "Facial Makeup Application Makeup Application Method Using the Same"; and
U.S. Pat. Appl. Pub. No. 2014/0209114 entitled "Device and Method for Applying Makeup."

SUMMARY

Embodiments of the present disclosure address needs, shortcomings, and limitations of existing convenience cosmetics. In accordance with embodiments of the present disclosure, a modular cosmetic system is provided; such modular cosmetic system provides a vast scope of possible formulas and mixtures that makes makeup accessible and affordable. Furthermore, such a modular cosmetic system provides consumers with options lacking in existing makeup lines; that is, such a modular cosmetic system provides a customizable cosmetics or makeup line that encompasses the totality of makeup functions and provides total control over purpose, color, and texture.

In accordance with at least one embodiment of the present disclosure, a modular makeup color system is disclosed and includes, but is not limited to, three main components. The three main components are (primary(ies), color(s), and modifier(s) that combine in multiple ways to create every kind of makeup of any color and texture customizable to the consumer's choosing. The primary(s) is finished makeup that is generally readily wearable as a powder, having a most versatile texture, and that can further be colored by mixing in color(s), if need be, and altered further in texture by mixing in modifier(s) to suit the purpose of the consumer. That is, as opposed to the "bases" of existing cosmetic lines that provide a predetermined makeup texture and severely limit the range and use of such product, by redefining a "base" as a primary(ies) and separating the texture component into a separate and distinct category (i.e., modifier(s)), a consumer can mix a single color that can function in any way the consumer desires. For example, a primary, a color, and a modifier may be mixed to produce the following non-limiting types of makeup: an eye shadow, an eyebrow shadow, an eyeliner, mascara, a contouring color, a foundation, a lip color, or anything additional the consumer may want for a color.

In accordance with embodiments of the present disclosure, such a modular cosmetic system may be considered as a mixing system of parts, and therefore it is possible to avoid complex chemical compositions and provide a consumer with complete control as to the ingredients; accordingly, the modular cosmetic system provides consumers with the following non-limiting options: vegan or non-vegan, gluten-free or not, dyes or pigments. Further, preservatives tend to be of high concern among consumers and organizations such as the Environmental Working Group; however, the preservative ingredients are most often used with the presence of water and therefore may be more susceptible to shorter shelf lives and may increase the likelihood of contamination. In accordance with embodiments of the present disclosure, the powders of primaries and colors included in the modular cosmetic system are dry and not premixed with water; accordingly, such powders and colors require less, if any, preservatives. Moreover, a consumer can opt against using a modifier(s). Alternatively, or in addition, the consumer may choose a blend of modifiers to decrease their potential sensitivity.

Placement of cosmetics on the face tends to follow established theories. There are many theories that pertain to or help a consumer achieve a desirous effect or result. The disclosure herein is neither focused nor directed to redefining or offering guidance with such theories. Rather, this disclosure provides, to the consumer, a function-based product that can do whatever it is the consumer may want, for whatever reason they want to, according to whatever cosmetic theory they may want to try.

In accordance with at least one embodiment of the present disclosure, a modular cosmetic system is provided, the modular cosmetic system including a primary component, a color component separate from the primary component, and a modifier component separate from the primary component and the color component. The primary component, color component, and modifier component may be mixable together to form at least one cosmetic product that can be applied to skin of a user.

Aspects of the modular cosmetic system further include a plurality of separate and distinct primary components, where the plurality of separate and distinct primary components includes a first primary component and a second primary component. Another aspect includes where the modular cosmetic system includes a plurality of separate and distinct color components and the plurality of separate and distinct color components includes a first color component and a second color component. In another aspect, an adhesion quality of the first primary component that is greater than an adhesion quality of the primary component. In yet another aspect, each of the first primary component and the second primary component of the modular cosmetic system includes a translucent material composition. Still further, another aspect of the modular cosmetic system includes a color of the first color component that is different from a color of the second color component. In yet another aspect, the modular cosmetic system the cosmetic product includes one part of the color component to about two parts of the primary component. In yet another aspect, the cosmetic product is at least one of a foundation, a concealer, an eye shadow, an eyeliner, or a blush. In another aspect, the modular cosmetic system includes a measuring device configured to measure at least one of the color component and the primary component. In still another aspect, the primary component is a tablet including perforated portions where each perforated portion of the primary component tablet corresponds to a predetermined first measurement amount. In still another aspect, the color component is a tablet including perforated portions, each perforated portion of the color component tablet corresponding to a predetermined second measurement amount. In yet another aspect, the predetermined first measurement amount is greater than the predetermined second measurement amount. An aspect of the modular cosmetic system includes a primary component that does not include mica.

In accordance with at least one embodiment of the present disclosure, a modular cosmetic system is provided, the system including a plurality of separate and distinct primary components, wherein the plurality of separate and distinct primary components includes a first primary component in powder form and a second primary component in powder form, a plurality of separate and distinct color components, wherein the plurality of separate and distinct color components includes a first color component in powder form and a second color component in powder form, a plurality of separate and distinct modifier components, wherein the plurality of separate and distinct modifier components includes a first modifier component in gel form and a second modifier in liquid form. The plurality of separate and distinct primary components, plurality of separate and distinct color components, and the plurality of separate and distinct modifier components may be mixable together to form at least one cosmetic product that can be applied to skin of a user.

It is an aspect of the modular cosmetic system where the cosmetic product is at least one of a foundation, a concealer, an eye shadow, an eyeliner, or a blush. In another aspect, the first primary component, first color component, and first modifier component are mixable together to form a foundation cosmetic product, and the first primary component, first color component, and first modifier component are mixable together to form an eyeliner.

In accordance with embodiments of the present disclosure, a method of making a cosmetic product is provided, the including providing a plurality of separate and distinct primary components, wherein the plurality of separate and distinct primary components includes a first primary component in powder form and a second primary component in powder form, providing a plurality of separate and distinct color components, wherein the plurality of separate and distinct color components includes a first color component in powder form and a second color component in powder form, and providing at least one modifier component. The plurality of separate and distinct primary components, plurality of separate and distinct color components, and the modifier component may be mixable together to form at least one cosmetic product that can be applied to skin of a user.

At least one aspect of the method includes mixing the first primary component and the first color component to form the at least one cosmetic product. At least one aspect of the method includes mixing the second primary component, the second color component, and the modifier component to form the at least one cosmetic product. In at least one aspect, the cosmetic product is at least one of a foundation, a concealer, an eye shadow, an eyeliner, or a blush.

This Summary is neither intended nor should it be construed as being representative of the full extent and scope of the present disclosure. The present disclosure is set forth in various levels of detail in the Summary as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive as to the patentable subject matter disclosed herein. Other benefits, embodiments, and/or characterizations of the present disclosure are possible utilizing, alone or in combination, the Summary as set forth above and/or described in the accompanying figures and/or in the description herein below. However, the Detailed Description of the Invention, the drawing figures, and the exemplary claim set forth herein, taken in conjunction with this Summary of the Invention, define the invention.

Additional features and advantages of embodiments of the present disclosure will become more readily apparent from the following description, particularly when taken together with the accompanying drawings.

BRIEF DESCRIPTION OF THE DRAWINGS

FIG. 4 illustrates an example of a mixing guide for mixing primaries and color in accordance with embodiments of the present disclosure;

DETAILED DESCRIPTION

Figure 1:
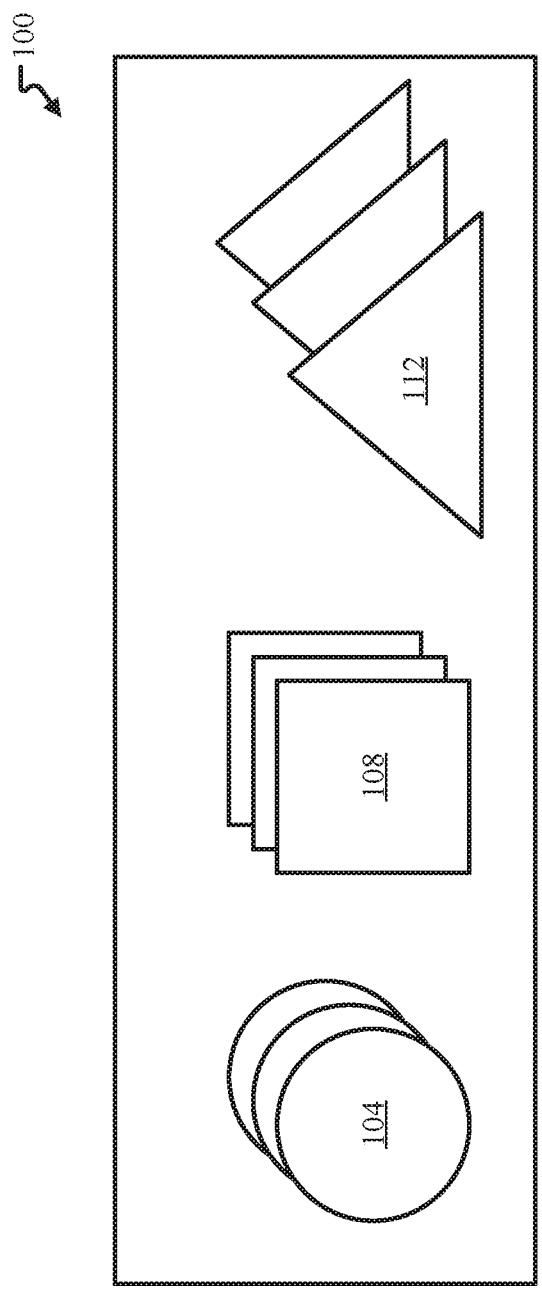
FIG. 1 illustrates an example of a modular cosmetics system in accordance with embodiments of the present disclosure.

In accordance with embodiments of the present disclosure, FIG. 1 illustrates a modular cosmetic system 100 including, but not limited to, a primary(ies) 104, color(s) 108, and modifier(s) 112. Each of the primary(ies) 104, color(s) 108, and modifier(s) 112 may interact with a consumer's skin to yield a variety of different optical illusion outcomes. For example, by systematically blending portions, or parts, of one or more of the primary(ies) 104, color(s) 108, and modifier(s) 112, a number of cosmetic/illusory effects on the skin may be achieved.

The primary(ies) 104 may be considered as the "base" of the modular cosmetic system 100; the primary(ies) 104 generally includes, but is not limited to, a translucent material composition having varying levels and/or actions of adhesion. In accordance with embodiments of the present disclosure, a second portion of the modular cosmetic system 100 is color(s) 108; color(s) 108 provides a range of colors of varying degrees in level, pigmentation, and densities that include neutral and rainbow colors and may or may not also effect the color of other cosmetic brands. In accordance with embodiments of the present disclosure, a third portion of the modular cosmetic system 100 includes the modifier(s) 112 which expand the reach of cosmetic textures when mixed with primary(ies) 104 and color(s) 108; the modifier(s) 112 may include but are not limited to, liquid, oily, sticky, waxy, creamy, and gel textures.

The range of products available from mixing the primary(ies) 104 and color(s) 108 covers the range of independent products available on the market in any cosmetic line (e.g., foundation, concealer, eye shadow, eyeliner, blush, primer, fallout veil, etc). The method of mixing the primary(ies) 104 and color(s) 108 may be by volume for ease of measuring/use and mixing in order to achieve results in accordance with the consumer's desired effect. As one example, the primary(ies) 104, color(s) 108, and modifier(s) 112 may be mixed dry in contained or closed bags which decreases the risk to the consumer of dust inhalation. In some embodiments, a measuring device may be provided that allows a consumer to easily measure the primary(ies) 104 and color(s) 108 by volume and further helps to keep each of the products bacteria free.

In accordance with at least one embodiment of the present disclosure, the use of modifier(s) (112) is dependent on the desired end result of the consumer. For example, the use of the modifier(s) 112 may alter the dispersal of the primary(ies) 104 having added color(s) 108 such that a thin or heavy dispersal of the primary(ies) 104 having added color(s) 108 may be achieved and therefore provide a varying illusory effect desired by the consumer.

As previously mentioned, and in accordance with at least one embodiment of the present disclosure, three parts, or portions, are included, where each part or portion has multiple purposes and actions, and are formulated to combine in varying parts by volume to produce multiple cosmetic products for many illusory effects upon the skin. Such is composed of dry, liquid, solid, and/or creamy ingredients that may or may not be blended, mixed, sifted, stirred, melted, grated, chilled, warmed, shaken, infused, emulsified, whisked, kneaded, merged, and/or layered. At least one part in the system is needed for an effect. In the description that follows, at least one part and/or portion presented is blended, mixed, sifted, stirred, pressed and/or heated.

In one aspect, the modular cosmetic system 100 allows for the convenience of access to every makeup effect. The modular cosmetic system 100 also allows for the immediate alteration of colors and effect for the moment of need. The modular cosmetic system 100 allows for open-ended purpose insofar as its scope of cosmetic coverage and illusory effect. The modular cosmetic system 100 provides the consumer more choices as to what ingredients they put on their skin and further diminishes the need for preservatives.

The present disclosure exhibits growth potential in new ways of cosmetic use by separating cosmetics into primary(ies) 104, color(s) 108, and modifier(s) 112, and mixing such portions into a final, or semi-final, mixture. In such an example, the modular cosmetic system 100 in FIG. 1 and the mixing ratios of FIG. 4 may be utilized to achieve every kind of makeup available on the market as individual products, such as foundation, eye shadow, blush, eyeliner, lip color, lash color, contouring, primers, fall-out veils, finishing powders, setting powders, concealers, contouring shades, or highlights; all these among the various kinds of stage makeup.

Figure 2A:
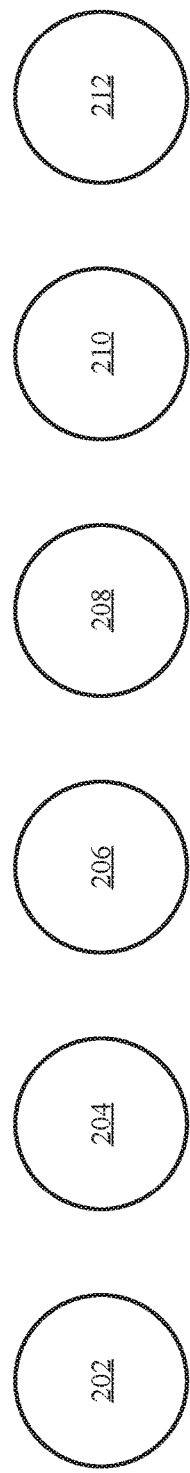
FIG. 2A illustrates an example of a primaries portion of the modular cosmetic system in accordance with embodiments of the present disclosure.

FIG. 2A depicts one or more primary(ies) 104 in accordance with embodiments of the present disclosure. As previously discussed, a primary(ies) 104 may be considered as a "base" of the modular cosmetic system 100. The primary(ies) 104 generally includes, but is not limited to, a translucent material composition having varying levels and/or actions of adhesion. Primary(ies) 104 tend to be finished makeup, makeup that is readily wearable as a powder and having a most versatile texture. Contrary to "bases" of existing cosmetic lines where the texture of the makeup is predetermined and severely limits the range and/or use of such product, the primary(ies) 104 may be customizable and can be colored and altered further in texture by mixing in color(s) 108 and modifier(s) 112 to suit the purpose of the consumer.

As further depicted in FIG. 2A, primary 202 and 208 are primaries 104 having adhesion qualities and a matte finish. Primaries 204 and 210 are primaries 104 having adhesion qualities and a low shine for a dewy effect. Because of the potential lightening/ashy effect of adhesive primaries 202, 204, 208, and 210 when mixed with color(s) 108, measuring and mixing is a relatively exact number, meaning there is room for error or intentional darkening or lightening/ashy effect but within parameters that ensure the quality of the mixtures' performance for true-to-color results. Primaries 206 and 212 are primaries without adhesion and without any alteration of color. Because primary 206 does not alter the color, a minimum amount of color(s) 108 is necessary for performance of the color, meaning a ratio of color 108 to these primary(ies) 104 could effectively be 1:10, or however much more it takes to get the desired end result; therefore, when mixing, as depicted in FIG. 4, the amount may be accompanied with a "+" to signify the open option of adding more primary 206 and/or 212. The packaging of the primaries 104 may include plastic zip bags to limit dust exposure. Alternatively, or in addition, the packaging of the primaries 104 may include pressing such primary(ies) 104 into perforated tablets and including the tablets in blister packaging.

Further, the primary(ies) 104 may determine shine and adhesion or the lack thereof, and optimal performance in regards to slip (the even distribution of color as it is applied to the skin; lack of stickiness), smoothness (non-abrasiveness), moisture balance for the skin, and translucency, which makes it color customizable, as opposed to the common idea of a makeup base that determines the texture and appropriate translucency/adhesion/slip for a specific color. Primary(ies) 104 may include a vegan or non-vegan matte primary which may be formulated for adhesion and spread quality, and a flat, smooth finish. The matte primary generally provides a solid, uniform spread that adheres colors to skin with a matte finish for f, etc. Primary(ies) 104 may include a vegan or non-vegan luster primary which may be formulated for adhesion and spread quality, and a dewy finish. That is, a luster primary may provide a solid, uniform spread that adheres colors to skin, but may provide a dewy finish for foundations, concealers, eye shadows, eyeliners, blushes, contouring colors, highlights, stage makeup, etc. Primary(ies) 104 may also be a vegan or non-vegan unattached primary, where such primary is formulated to not adhere at all to skin, but is formulated for buffering color disbursement over the skin and/or to trap and to remove excess moisture from the skin. That is, an unattached primary does not adhere to the skin as do matte and luster primaries. Because an unattached primary absorbs moisture and oil and then falls away, it is often the choice for fallout veils and touchup powders. When mixed with colors, an unattached primary will lower the concentration of pigment on the skin without altering the colors (great for the most sensitive skin types when added to your finished formula; it also helps to absorb oils through the day when added to a foundation formula). Because the unattached primary does not alter the colors, mixing of the unattached primary with color(s) 108 and/or modifier(s) 112 does not have to be in equal parts. For example, if a consumer wants a lightly tinted touchup powder, a tiny bit of color(s) 108 will go a long way with an unattached primary. When applied to the skin alone, an unattached primary will dust away without leaving any effect (lightening or color or otherwise) on the skin.

In terms of primary(ies) 104, a primary(ies) 104 may include a mixture of one or more ingredients to achieve a desired shine, adhesion, and performance with regard to slip, smoothness, moisture balance of the skin, and translucency. For example, a matte non-vegan primary may include, but is not limited to, nylon 12, rice, calcium carbonate, kaolin, silk, magnesium myristate, and silica microspheres. A luster non-vegan primary may include, but is not limited to, nylon 12, rice, calcium carbonate, kaolin, silk, magnesium myristate, silica microspheres, and mica. An unattached non-vegan primary may include, but is not limited to rice, calcium carbonate, and silk. A matte vegan primary may include, but is not limited, to nylon 12, rice, calcium carbonate, kaolin, magnesium myristate, and silica microspheres. A luster vegan primary may include, but is not limited to, mica, nylon 12, rice, calcium carbonate, kaolin, magnesium myristate, and silica microspheres. An unattached vegan primary may include, but is not limited to, rice, calcium carbonate, and kaolin. As provided in Tables 1-6, an amount of an ingredient, by volume, for example primaries, is provided in accordance with embodiments of the present disclosure. The disclosed range of each ingredient is intended to encompass and include about the lower amount of the range value, each amount between the range, and/or about the upper amount of the range value. For example, a range disclosed as including 25% to 35% may include about 25%, about 35%, 25%, 26%, 27%, 28%, 29%, 30%, 31%, 32%, 33%, 34%, and/or 35%. Alternatively, or in addition, Tables 1-6 provide an amount of an ingredient, by weight, in accordance with embodiments of the present disclosure. The disclosed range of each ingredient is intended to encompass and include about the lower amount of the range value, each amount between the range, and/or about the upper amount of the range value. For example, a range disclosed as including 25% to 35% may include about 25%, about 35%, 25%, 26%, 27%, 28%, 29%, 30%, 31%, 32%, 33%, 34%, or 35%.

TABLE 1

Matte (Non-Vegan)

| | |
|---|---|
| nylon 12 | 35% to 45% |
| rice | 29% to 39% |
| calcium carbonate | 12% to 22% |

TABLE 1-continued

Matte (Non-Vegan)

| | |
|---|---|
| kaolin | 1% to 10% |
| silk | .5% to 5% |
| magnesium myristate | .2% to 3% |
| silica microspheres | .2% to 3% |

TABLE 2

Luster (Non-Vegan)

| | |
|---|---|
| nylon 12 | 5% to 15% |
| rice | 1% to 10% |
| calcium carbonate | 1% to 10% |
| kaolin | 1% to 10% |
| silk | .5% to 5% |
| magnesium myristate | .2% to 3% |
| silica microspheres | .2% to 3% |
| mica | 60% to 80% |

TABLE 3

Unattached (Non-Vegan)

| | |
|---|---|
| rice | 40% to 60% |
| calcium carbonate | 40% to 60% |
| silk | .5% to 5% |

TABLE 4

Matte (Vegan)

| | |
|---|---|
| nylon 12 | 35% to 45% |
| rice | 29% to 39% |
| calcium carbonate | 12% to 22% |
| kaolin | 1% to 10% |
| magnesium myristate | .2% to 3% |
| silica microspheres | 2.% to 3% |

TABLE 5

Luster (Vegan)

| | |
|---|---|
| mica | 60% to 80% |
| nylon 12 | 5% to 15% |
| rice | 1% to 11% |
| calcium carbonate | 1% to 10% |
| kaolin | 1% to 11% |
| magnesium myristate | .2% to 3% |
| silica microspheres | .2% to 3% |

TABLE 6

Unattached (Vegan)

| | |
|---|---|
| rice | 40% to 60% |
| calcium carbonate | 40% to 60% |
| kaolin | .5% to 5% |

Figure 2B:
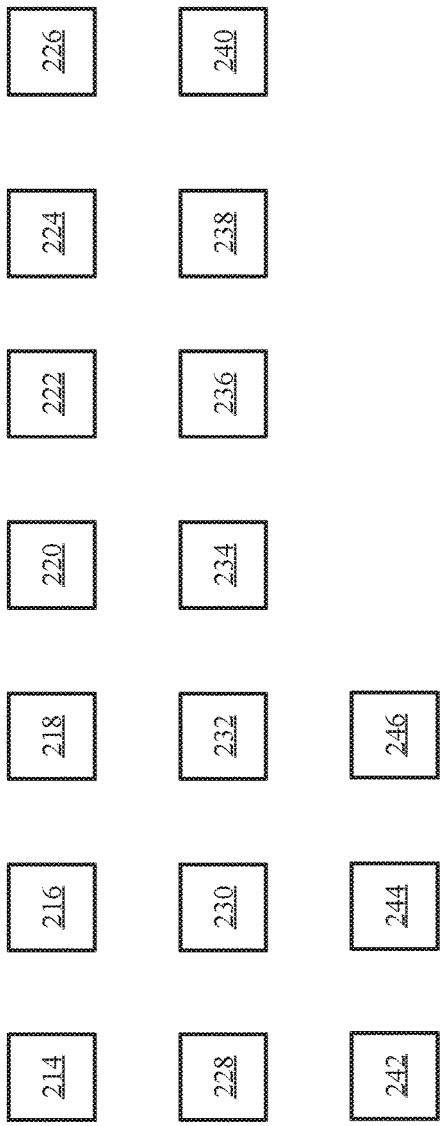
FIG. 2B illustrates an example of a colors portion of the modular cosmetic system in accordance with embodiments of the present disclosure.

One or more colors 108 are depicted in FIG. 2B in accordance with embodiments of the present disclosure. The color(s) 108 may be materials that are true-to-color in appearance, formulated to mix and be worn with primary(ies)108 so that the color of the resulting mixture remains true when worn on the skin. Alternatively, or in addition, the color(s) 108 may be materials that are true-to-color in appearance, formulated to mix and be worn only with primary(ies)108 so that the color of the resulting mixture remains true when worn on the skin. The color(s) 108 may include neutrals (e.g., N) which are coloring materials that include neutral tones in varying levels of lightness that range from black to white. Neutrals may have an undertone that tends to be more on the yellow spectrum, but can be adjusted by using other color(s) 108, such as rainbow colors of red, yellow, green, blue, red, and/or orange for example. The rainbow colors may be coloring materials that represent the colors of the Color Theory, or color chart, and are the colors that one's eyes perceive that are not neutral. Non-neutral color(s) 108 are not limited to one tone of a single color, but range the spectrum from secondary, tertiary, and so on.

Ingredients a user is sensitive to, such as mica. may be excluded from the primary. Alternatively, or in addition, an amount of the ingredient, such as mica, may be reduced when compared to conventional cosmetic products. Moreover, an amount of ingredient, such as mica, may be customizable based on a user's preferences. For example, a user may vary an amount and/or type of primary based on a sensitivity to the ingredients in the primary while still achieving a desired function and look of the cosmetic product.

The color(s) 108 part of the modular cosmetic system 100 is depicted in FIG. 2B. Color 214 is a sparkle product that can be intermixed with other colors 108 or can be mixed alone with a primary(ies) 104. The neutral color level series ranges from level one, color 216, the darkest level which is black, to level twelve, 228, the absence of color which is white. Color 218 is heavily pigmented to the darkest neutral color achievable with the mineral ingredients of the modular cosmetics system 100. Color 220 is also heavily pigmented to achieve a lighter neutral on the darker side of the color level spectrum. Color 222 is a medium pigmented neutral, and colors 224 and 226 are light to lightest neutrals. Colors 230 to 246 represent the rainbow colors, all of which are heavily pigmented, but because of the physical nature of the ingredients required to create some of the rainbow colors 230-246, some of the rainbow colors are mixed with less primary(ies) 104, than others. The amount of pigmentation and the varying densities of the color(s) 108, factor into the measuring and mixing method as will be described. For example, the heavier the pigmentation, the stickier the color(s) 108 absent the primary(s) 104. While the lighter pigmented color(s) may not stick and smear on the skin without the addition of primary(s) 104, the measuring parameters of the primary(ies) 104 must still be met to ensure even, smooth, reliable results.

In terms of color(s) 108 composition, a color(s) 108 may include a mixture of one or more ingredients to achieve a desired color and/or effect. For example, a sparkle color may include, but is not limited to, nylon 12, calcium carbonate, and Micro-fine Glitter. A black (1N) color may include, but is not limited to, nylon 12, calcium carbonate, and black iron oxide. A 2N neutral color may include, but is not limited to, nylon 12, calcium carbonate, yellow iron oxide, red iron oxide, and black iron oxide. A 4N neutral color may include, but is not limited to nylon 12, calcium carbonate, yellow iron oxide, brown iron oxide, and black iron oxide. A 6N, 8N, and 10N neutral color may include, but is not limited to, zinc, calcium carbonate, yellow iron oxide, and brown iron oxide. A white color may include, but is not limited to, zinc and calcium carbonate. A red color may include, but is not limited to, nylon 12, calcium carbonate, and Red Iron Oxide. A blue color may include, but is not limited to, calcium carbonate, nylon 12, and Ultramarine Blue. A yellow color may include, but is not limited to, calcium carbonate, nylon 12, and yellow iron oxide. A green color may include, but is not limited to, nylon 12, calcium carbonate, and chromium oxide green matte. A bright red color may include, but is not limited to, nylon 12, calcium carbonate, and carmine. A purple color may include, but is not limited to, nylon 12, calcium carbonate, and manganese violet. A bright yellow color may include, but is not limited to, nylon 12, calcium carbonate, and Yellow #5. A dark blue color may include, but is not limited to, nylon 12, calcium carbonate, and ferric ferrocyanide. An orange color may include, but is not limited to, nylon 12, calcium carbonate, Carmine, and yellow iron oxide. As provided in Tables 7-22, an amount of an ingredient, by volume, for example colors, is provided in accordance with embodiments of the present disclosure. The disclosed range of each ingredient is intended to encompass and include about the lower amount of the range value, each amount between the range, and/or about the upper amount of the range value. For example, a range disclosed as including 25% to 35% could include about 25%, about 35%, 25%, 26%, 27%, 28%, 29%, 30%, 31%, 32%, 33%, 34%, and/or 35%. Alternatively, or in addition, Tables 7-22 provide an amount of an ingredient, by weight, in accordance with embodiments of the present disclosure. The disclosed range of each ingredient is intended to encompass and include about the lower amount of the range value, each amount between the range, and/or about the upper amount of the range value. For example, a range disclosed as including 25% to 35% may include about 25%, about 35%, 25%, 26%, 27%, 28%, 29%, 30%, 31%, 32%, 33%, 34%, or 35%.

TABLE 7

0 Sparkle

| | |
|---|---|
| nylon 12 | 25% to 35% |
| calcium carbonate | 10% to 25% |
| micro-fine glitter | 45% to 60% |

TABLE 8

1N Black

| | |
|---|---|
| nylon 12 | 25% to 35% |
| calcium carbonate | 10% to 25% |
| black iron oxide | 45% to 60% |

TABLE 9

2N

| | |
|---|---|
| nylon 12 | 25% to 35% |
| calcium carbonate | 2% to 12% |
| yellow iron oxide | 7% to 17% |
| red iron oxide | 1% to 9% |
| black iron oxide | 40% to 55% |

TABLE 10

4N

| | |
|---|---|
| nylon 12 | 25% to 35% |
| calcium carbonate | 2% to 12% |
| yellow iron oxide | 15% to 25% |
| brown iron oxide | 15% to 25% |
| black iron oxide | 15% to 25% |

TABLE 11

6N

| | |
|---|---|
| zinc | 50% to 68% |
| calcium carbonate | 20% to 32% |
| yellow iron oxide | 1% to 13% |
| brown iron oxide | 1% to 13% |

TABLE 12

8N

| | |
|---|---|
| zinc | 60% to 80% |
| calcium carbonate | 15% to 32% |
| yellow iron oxide | 1% to 5% |
| brown iron oxide | 1% to 5% |

TABLE 13

10N

| | |
|---|---|
| zinc | 70% to 90% |
| calcium carbonate | 8% to 24% |
| yellow iron oxide | 1% to 3% |
| brown iron oxide | 1% to 3% |

TABLE 14

White

| | |
|---|---|
| zinc | 60% to 85% |
| calcium carbonate | 15% to 40% |

TABLE 15

Red

| | |
|---|---|
| nylon 12 | 20% to 40% |
| calcium carbonate | 1% to 12% |
| red iron oxide | 50% to 70% |

TABLE 16

Blue

| | |
|---|---|
| calcium carbonate | 1% to 12% |
| nylon 12 | 20% to 40% |
| ultramarine blue | 50% to 70% |

TABLE 17

Yellow

| | |
|---|---|
| calcium carbonate | 30% to 50% |
| nylon 12 | 20% to 40% |
| yellow iron oxide | 20% to 40% |

TABLE 18

Green

| | |
|---|---|
| nylon 12 | 20% to 40% |
| calcium carbonate | 10% to 21% |
| chromium oxide green matte | 45% to 63% |

TABLE 19

Bright Red

| | |
|---|---|
| nylon 12 | 20% to 40% |
| calcium carbonate | 10% to 21% |
| carmine | 50% to 70% |

TABLE 20

Purple

| | |
|---|---|
| nylon 12 | 20% to 40% |
| calcium carbonate | 10% to 21% |
| Manganese violet | 45% to 63% |

TABLE 21

Dark Blue

| | |
|---|---|
| nylon 12 | 20% to 40% |
| calcium carbonate | 10% to 21% |
| Ferric ferrocyanide | 45% to 63% |

TABLE 22

Orange

| | |
|---|---|
| nylon 12 | 20% to 40% |
| calcium carbonate | 10% to 21% |
| carmine | 7% to 18% |
| yellow iron oxide | 30% to 50% |

Figure 2C:
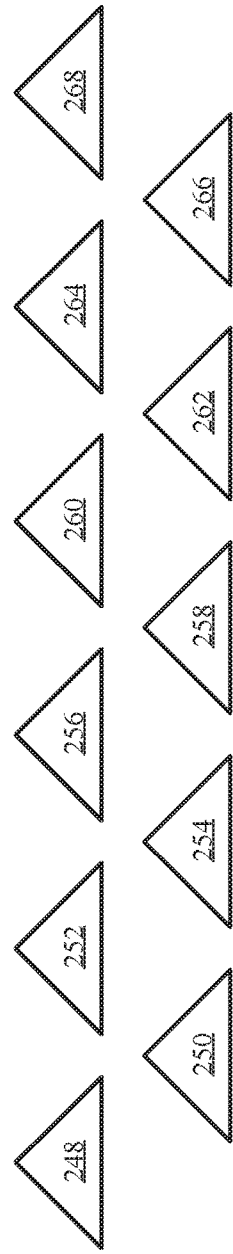
FIG. 2C illustrates an example of a modifiers portion of the modular cosmetic system in accordance with embodiments of the present disclosure.

One or more modifier(s) 112 are depicted in FIG. 2C, in accordance with embodiments of the present disclosure. The modifier(s) 112 offer texture and application variation. The modifier(s) 112 may include cake, cream, liquid; heavy, light, or airbrush thin type textures. Modifier(s) 112 may include, but are not limited to, a favorite moisturizer, oil, such as jojoba or coconut, or other modifier(s) listed herein.

As further depicted in FIG. 2C, 248, 250, and 252 represent liquid modifiers that are dispensed from dropper bottles. Modifier(s) 254, 256, 258, and 260 represent anhydrous modifiers of varying stiffness dispensed from squeeze tubes. 262, 264, and 266 represent emulsion modifiers of varying viscosity, and modifier 268 represents a gel Modifier. The modifiers may be mixed in any quantity and therefore are not necessarily part of a mixing recipe or included on a mixing chart because there is no minimum or maximum measurement. The amount of modifier(s) and which modifier(s) to use is very much consumer dependent, as the amount depends on the consumer's needs to achieve the desired illusory result. For example, the smallest amount of modifier 248, to any mix of primary(ies) 104 and/or color(s) 108 may enhance the vibrancy of the color 108, but a large amount of modifier 248 to a mix of primary(ies) 104 and/or color(s) 108 may disperse the makeup such that it is thin enough to be used in an airbrush machine and will need to build up in layers to achieve the most vibrancy.

In terms of a modifier(s) (112), a modifier(s) 112 may include a mixture of one or more ingredients to achieve a desired alteration to texture and disbursement of the primary(ies) 104 and/or color(s) 108. For example, a vegetable modifier may include, but is not limited to, water and glycerin. A silicone modifier may include, but is not limited to water, glycerin, dimethiconde, cyclomethicone, hydroxyethylcellulose, and a preservative such as one or more of phenoxyethanl, paraben, and borax (sodium borate, sodium tetraborate, or disodium tetraborate). An oil modifier may include, but is not limited to, neem oil, coconut oil, and lemongrass. A soft wax modifier may include, but is not limited to, dionized water, beeswax, carnauba or rice bran wax, stearic acid, triethanolamine (TEA), candlile, dermacryl 79, cocoa butter, preservative, glycerin, and cetyl alcohol. A stiff wax modifier may include, but is not limited to, beeswax, cocoa butter, carnauba or rice bran wax, glycerin, caster oil, jojoba, water, and stearic acid. A cream modifier may include, but is not limited to, jojoba, vitamin E oil, rice bran wax or carnauba, water, stearic acid, and a preservative. A gel modifier may include, but is not limited to, water xanthan gum, grapeseed oil, and a preservative. As provided in Tables 23-37, an amount of an ingredient, by volume, for example modifiers, is provided in accordance with embodiments of the present disclosure. The disclosed range of each ingredient is intended to encompass and include about the lower amount of the range value, each amount between the range, and/or about the upper amount of the range value. For example, a range disclosed as including 25% to 35% could include about 25%, about 35%, 25%, 26%, 27%, 28%, 29%, 30%, 31%, 32%, 33%, 34%, and/or 35%. A percentage to the right of the semicolon is a disclosed percentage for a first embodiment of the corresponding modifier. Alternatively, or in addition, Tables 23-37 provide an amount of an ingredient, by weight, in accordance with embodiments of the present disclosure. The disclosed range of each ingredient is intended to encompass and include about the lower amount of the range value, each amount between the range, and/or about the upper amount of the range value. For example, a range disclosed as including 25% to 35% may include about 25%, about 35%, 25%, 26%, 27%, 28%, 29%, 30%, 31%, 32%, 33%, 34%, or 35%. A percentage to the right of the semicolon is a disclosed percentage for a first embodiment of the corresponding modifier.

TABLE 23

Vegetable Modifier

| | |
|---|---|
| Water | 60% to 75%; 69.6% |
| glycerin | 25% to 37%; 30% |
| citric acid | .1% to .3%; .2% |
| potassium sorbate | .1% to .3%; .2% |

TABLE 24

Silicone Modifier

| | |
|---|---|
| water | 70% to 85%; 77.55% |
| hydroxyethylcellulose | 1% to 3%; 2% |
| glycerin | 1% to 10%; 5% |
| citric acid | .1% to .3%; .2% |
| potassium sorbate | .1% to .3%; .2% |
| dimethicone | 1% to 9%; 4.68% |
| cyclomethicone | 5% to 15%; 9.37% |
| preservative (Phenoxyethanol, Paraben, Borax) | .2% to 2%; 1% |

TABLE 25

Oil Modifier

| | |
|---|---|
| hemp oil | 30% to 40%; 35% |
| castor oil | 30% to 40%; 35% |
| Sunflower oil | 24% to 34%; 29% |
| phenoxyethanol | .1% to 2%; 1% |

TABLE 26

Wax: Soft Modifier

| | |
|---|---|
| deionized water | 55% to 70% |
| beeswax | 2% to 8% |
| carnauba or rice bran wax | 2% to 5% |
| stearic acid | 2% to 6% |
| triethanolamine (TEA) | 1% to 5% |
| candelile | 2% to 8% |
| dermacryl 79 | 2% to 8% |
| cocoa butter | 1% to 5% |
| preservative | 2% to 5% |
| glycerin | 1% to 3% |
| cetyl alcohol | .5% to 3% |

TABLE 27

Wax: Stiff Modifier

| | |
|---|---|
| beeswax | 12% to 23% |
| cocoa butter | .5% to 5% |
| carnauba or rice bran wax | 10% to 20% |
| glycerin | 3% to 13% |
| caster oil | 10% to 20% |
| jojoba | 10% to 20% |
| water | 15% to 25% |
| stearic acid | 3% to 13% |

TABLE 28

Anhydrous Level (AL) 1: Hard

| | |
|---|---|
| hemp seed oil | 27% to 37%; 31.95% |
| polyisbutene 1200 | 8% to 18%; 13.25% |
| beeswax | 13% to 23%; 17.99% |
| candelilla | 19% to 29%; 23.99% |
| sunflower wax | 2% to 13%; 7.81% |
| lanolin | 1% to 8%; 3.91% |
| citric acid | .05% to .2%; .1% |
| Phenoxyethanol | .2% to 2%; 1% |

TABLE 29

Anhydrous Level (AL) 2: Stiff

| | |
|---|---|
| hemp seed oil | 27% to 37%; 31.85% |
| polyisbutene 1200 | 19% to 29%; 23.96% |
| beeswax | 13% to 23%; 17.38% |
| candelilla | 9% to 19%; 13.99% |
| sunflower wax | 1% to 8%; 3.91% |
| lanolin | 2% to 13%; 7.81% |
| citric acid | .05% to .2%; .1% |
| Phenoxyethanol | .2% to 2%; 1% |

TABLE 30

Anhydrous Level (AL) 3: Slick

| | |
|---|---|
| hemp seed oil | 28% to 38%; 33.95% |
| polyisbutene 1200 | 20% to 30%; 24.95% |
| beeswax | 23% to 32%; 28.38% |
| sunflower wax | 1% to 9%; 3.91% |
| lanolin | 2% to 13%; 7.81% |
| Phenoxyethanol | .2% to 2%; 1% |

TABLE 31

Anhydrous Level (AL) 2: Stiff

| | |
|---|---|
| hemp seed oil | 27% to 37%; 31.95% |
| polyisbutene 1200 | 19% to 29%; 23.96% |
| beeswax | 3% to 13%; 8% |
| candelilla | 9% to 19%; 14% |
| sorbitan stearate | 1% to 6%; 3% |
| sunflower wax | 1% to 8%; 3.91% |
| lanolin | 2% to 13%; 7.81% |
| citric acid | .05% to .2%; .1% |
| Phenoxyethanol | .2% to 2%; 1% |
| glycerin | 1% to 11%; 6.27% |

TABLE 32

Cream Modifier

| | |
|---|---|
| jojoba | 10% to 20% |
| vitamin E oil | 2% to 6% |
| rice bran wax or carnauba | .5% to 3% |
| water | 60% to 80% |
| stearic acid | 3% to 11% |
| preservative | 1% to 5% |

TABLE 33

Silicone Cream Modifier

| | |
|---|---|
| Distilled water | 60% to 72%; 67.6% |
| Citric acid | .05% to 2%; .2% |
| Potassium sorbate | .05% to 2%; .2% |
| Hydroxyethylcellulose | .1% to 2%; 1% |
| glycerin | 1% to 10%; 5% |
| Polyglyceryl-4-oleate | 5% to 15%; 10% |
| dimethicone | 1% to 10%; 5% |
| cyclomethicone | 5% to 15%; 10% |
| phenoxythexanol | .1% to 2%; 1% |
| preservative | 1% to 5% |

TABLE 34

Thick Cream/Cake

| | |
|---|---|
| distilled water | 25% to 35%; 30% |
| hemp seed oil | 37% to 47%; 42.16% |
| sorbitan stearate | 5% to 15%; 10% |
| beeswax | 11% to 21%; 16.54% |
| citric acid | .05% to 2%; .1% |
| phenoxythexanol | .1% to 2%; 1% |
| potassium stearate | .05% to 2%; .2% |

TABLE 35

Thick Cream/Cake

| | |
|---|---|
| distilled water | 65% to 85%; 76.4% |
| hemp seed oil | 2% to 12%; 8% |
| sorbitan stearate | 5% to 15%; 10% |
| beeswax | 1% to 9%; 4.22% |
| citric acid | .05% to 2%; .1% |
| phenoxythexanol | .1% to 3%; 1% |
| potassium stearate | .05% to 2%; .2% |

TABLE 36

Gel Modifier

| | |
|---|---|
| water | 75% to 90% |
| xanthan gum | .5% to 2% |
| grapeseed oil | 5% to 15% |
| preservative | .5% to 2% |

TABLE 37

Gel Modifier II

| | |
|---|---|
| Distilled water | 60% to 77%; 67.55% |
| Hydroxyethylcellulose | .05% to 5%; .2% |
| Glycerin | 1% to 10%; 5% |
| Citric Acid | .05% to 2%; .2% |
| Potassium Sorbate | .05% to 2%; .2% |

Figure 3:
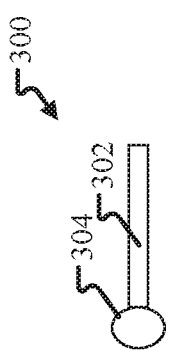
FIG. 3 illustrates an example of a measuring device used for mixing varying volumes of primaries, colors, and/or modifiers in accordance with embodiments of the present disclosure.

A measuring device 300 is depicted in FIG. 3 in accordance with embodiments of the present disclosure. The measuring device 300 generally includes a handle 302 and a measuring portion 304. The measuring device 300 generally prevents physical handling of ingredients such as primary(ies) 104 and color(s) 108 and provides ease in making measurements in accordance with FIG. 4.

FIG. 4 depicts one or more recommended ratios for mixing primary(ies) 104 with color(s) 108 in accordance with embodiments of the present disclosure. Primary(ies) 104 and color(s) 108 are formulated to be mixed together in parts. If matte or luster are to be mixed, mixing according to the chart will achieve true level results. More matte and/or luster than color(s) 108 could result in a lighter, ashy appearance (unattached is a little different as it may not alter the color(s) 108; therefore, the color(s) 108 parts can be much less). More color(s) 108 than primary 104 may result in heavy, patchy results on skin. Using the measuring device 300, the primary(ies) 104 and color(s) 108 of correct proportions can be measured and then mixed.

Figure 5A:
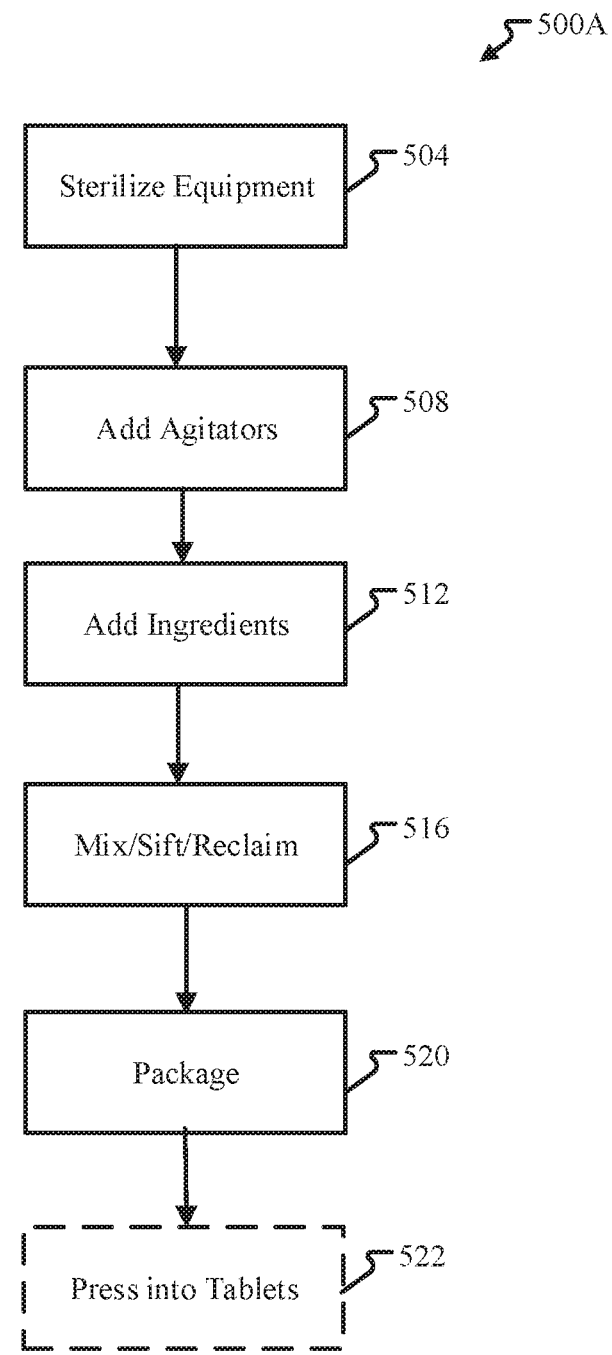
FIG. 5A illustrates a first flow chart directed to a method of mixing primaries and/or colors in accordance with embodiments of the present disclosure.

FIG. 5A depicts a flowchart of a method for the preparation of a primary(ies) 104 and/or color(s) 108 in accordance with embodiments of the present disclosure. The method 500A may begin at step 504 where all equipment necessary in the production of the particular primary 104 and/or color 108 is sterilized. Sterilization may include wiping, soaking, and/or heating such equipment to effectively remove contaminants. At step 508, agitators may be added to a mixing vessel; for example, glass balls numbering in the range of five to fifteen may be added to the mixing vessel. At step 512, ingredients are added to the mixing vessel. For example, if a 6N color is being mixed, zinc, calcium carbonate, yellow iron oxide, and brown iron oxide are measured and then added to the mixing vessel. At step 516, the ingredients may be mixed, sifted, and reclaimed. For example, the mixed ingredients may be sifted onto wax paper, collected, and then packaged at step 520. At step 522, the collected ingredients may then be optionally pressed into tablets.

Figure 5B:
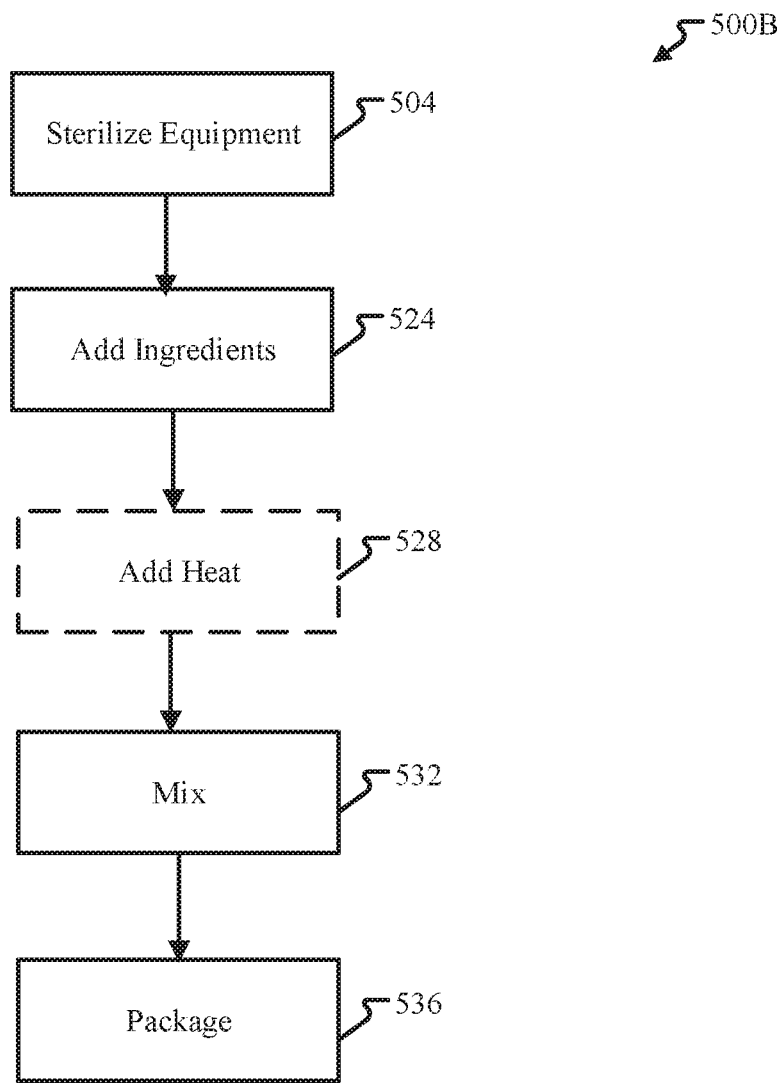
FIG. 5B illustrates a second flow chart directed to a method of mixing modifiers in accordance with embodiments of the present disclosure.

FIG. 5B depicts a flowchart of a method for the preparation of a modifier 112 in accordance with embodiments of the present disclosure. The method 500B may begin at step 504 where all equipment necessary in the production of the modifier 112 is sterilized. Sterilization may include wiping, soaking, and/or heating such equipment to effectively remove contaminants. At step 524, ingredients may be added to a mixing vessel. Optionally, heat may be applied to one or more ingredients at step 528. At step 532, the ingredients are mixed and then packaged into a container at step 536 and/or further mixed via shaking.

Figure 6:
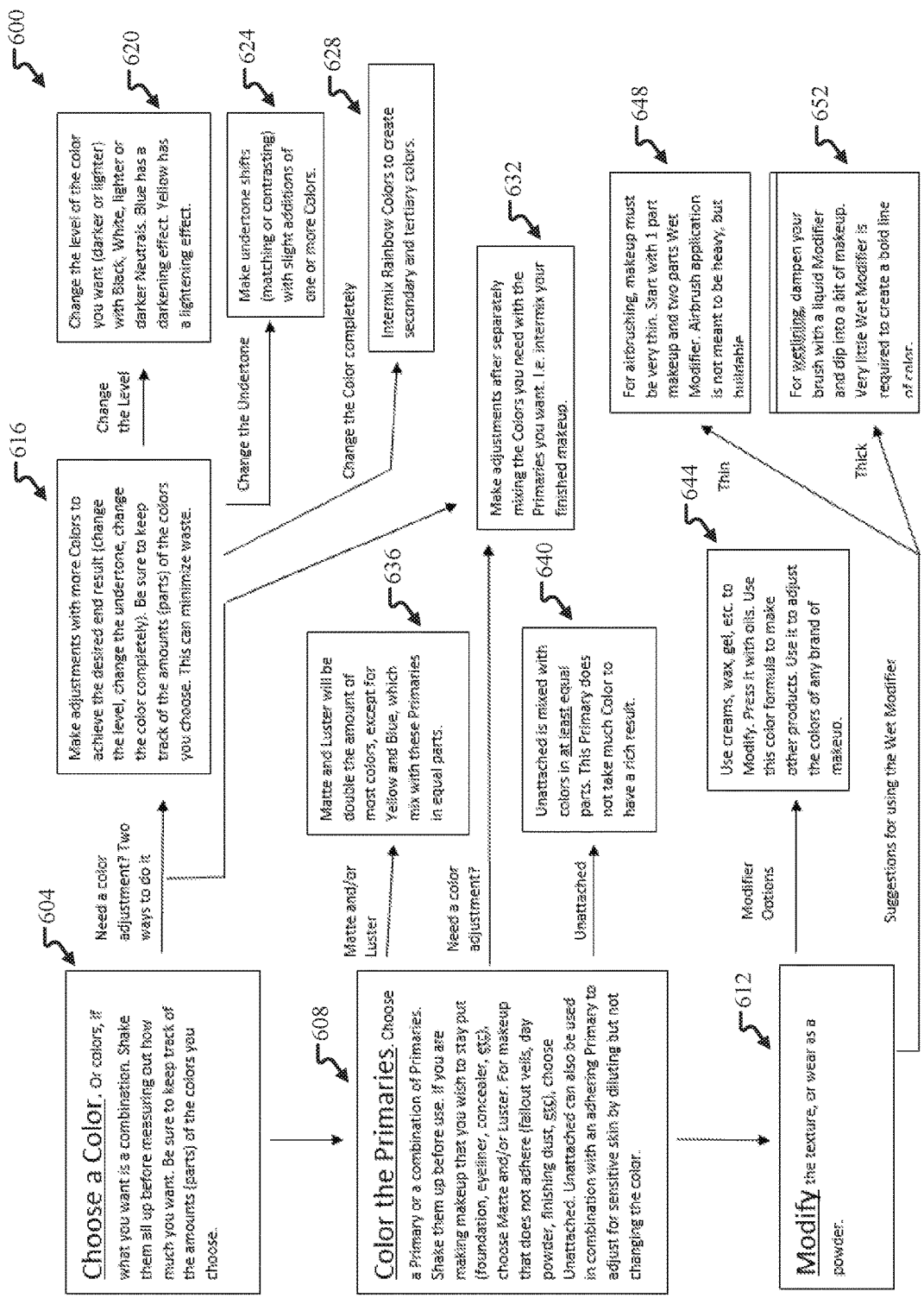
FIG. 6 illustrates a third flow chart directed to a method of mixing primaries, colors, and/or modifiers in accordance with embodiments of the present disclosure.

FIG. 6 depicts a method 600 for mixing primary(ies) 104, color(s) 108, and modifier(s) 112 in accordance with embodiments of the present disclosure. At step 604, a color 108 is chosen. It is noted that multiple colors 108 may be mixed together to achieve a desired color. However, in some mixtures, the primary 104 and modifier 112 may impact the final end mixture color. At step 608, the chosen color 108 or colors 108 are added to one or more primaries 104. That is, at step 608, one or more primaries 104 are chosen based on a desired end product and/or effect and the previously chosen colors 108 are added to the chosen primary(ies) 104. At step 612, a modifier 112 may be added to the primary 104 and color 108 mixture to alter a texture of the primary 104 and color 108 mixture.

It should be noted that adjustments to color 108 may be made in accordance with steps 612-632, and that such steps may be repeated if necessary. That is, at step 616, a consumer may choose to alter a level, undertone, or the color entirely for example. Thus, at step 620, a level may be changed by adding one or more neutrals for example to darken or lighten the resulting color mixture. Alternatively, or in addition, other rainbow colors may be utilized to lighten or darken the resulting color mixture. At step 624, undertone shifts may be performed by slightly adding one or more matching and/or contrasting colors. In accordance with at least one embodiment, the resulting color can be completely changed by intermixing rainbow colors to create secondary and tertiary colors, as provided at step 628.

FIG. 6 also provides additional detail with respect to mixing and achieving a desired primary. For example, matte and luster primaries, when mixed with most colors, will most likely need double the amount of color, whereas when mixed with yellow and blue colors, the ratio is closer to one-to-one, as illustrated at step 636. For unattached primaries, the primary and color are generally mixed in a one-to-one ratio, where less than a one-to-one ratio may also produce satisfactory results, as illustrated at step 640. At step 632, the resulting colored primary may be adjusted with more color, other colors, and/or other makeup products.

In accordance with embodiments of the present disclosure, the modifier(s) 112 may be mixed into the colored primary resulting from step 608. Creams, wax, and/or gel modifiers may be used to alter texture and function as illustrated at step 644. In some embodiments, the modifier may be added to alter texture, function, and/or color of other makeup products. At step 648, a modifier may be added directly to the colored primary mixture for use in airbrushing applications. Alternatively, or in addition, at step 652, the modifier may be added to a cosmetic applicator prior to dipping the cosmetic applicator in the colored primary mixture.

The flow chart depicted in FIG. 6 can generally be used to mix any kind of makeup. As further provided in the U.S. Provisional Patent Application Ser. No. 62/266,140, filed Dec. 11, 2015, such a procedure may be used to mix blush, concealer, lipstick, eyeliner, day powder, primer, eye shadow, and any other type of cosmetic using various recommended ratios of primaries, colors, and modifiers.

Figure 7:
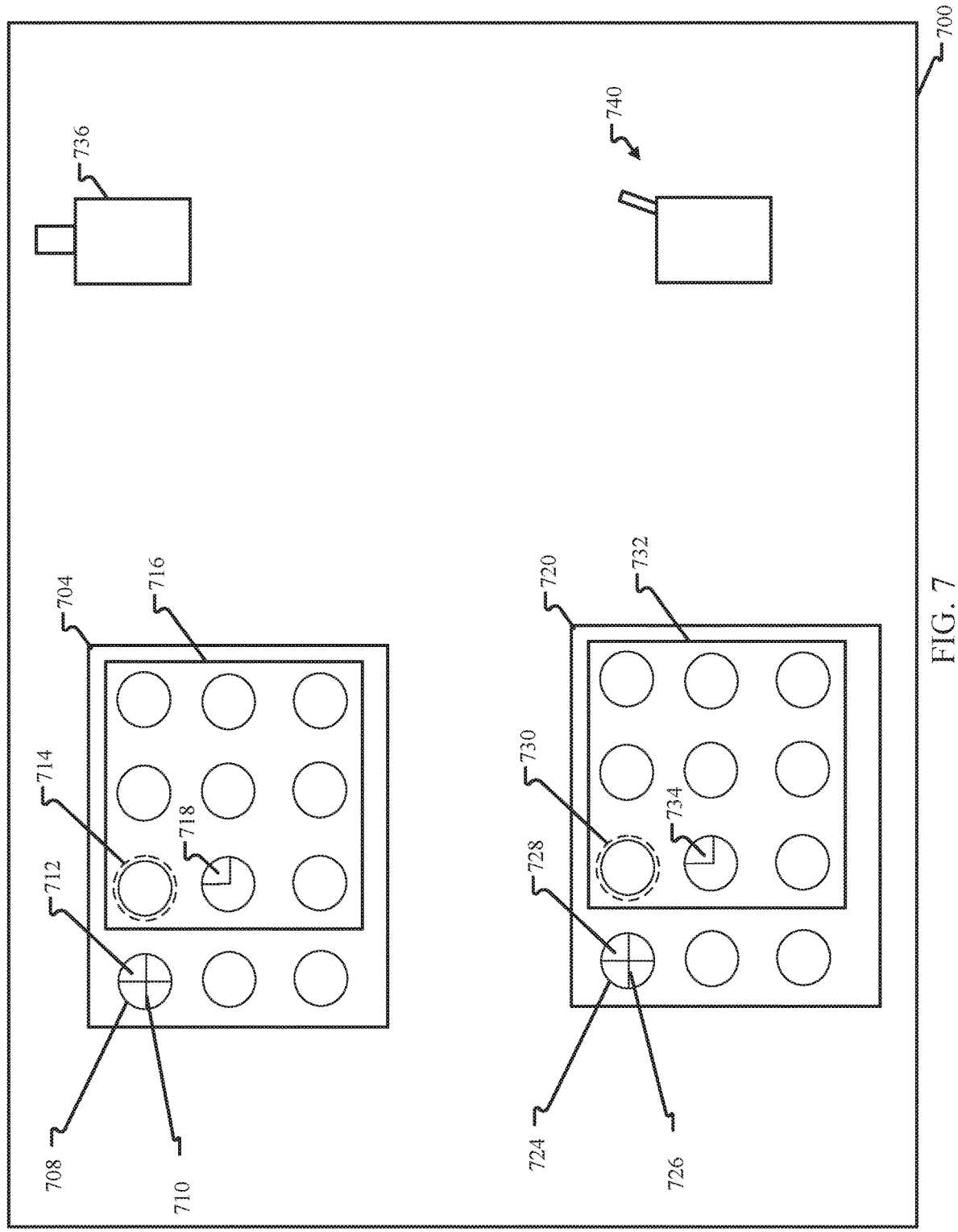
FIG. 7 illustrates an example of a modular cosmetics kit in accordance with embodiments of the present disclosure.

FIG. 7 is an example of a modular cosmetics kit 700 in accordance with embodiments of the present disclosure. The modular cosmetics kit 700, may include, but is not limited to, a package of primaries 704, a package of colors 720, a modifier 736, and/or a mixing tool 740, such as a mortar and pestle. The package of primaries 704 generally include tablets 708 packaged in blister packaging with perforations 710 for easy measuring and making adjustments to a mixture. For example, if a primary is needed for sensitive skin, a quarter of the primary 712 can be used instead of the whole tablet 708 of primary. The packaging itself can also have perforations 714 around each tablet 708 for ease of use, and ideally, the peel-off backing 716 may reseal such that other portions 718 of a tablet 708 may be utilized at a later point in time. The package of primaries 704 may include one or more primary(ies) 104, matte, luster, and/or unattached, and/or combinations thereof, pressed into tablets 708. The quantity of each tablet 708 may be double an amount of a color per the mixing instructions depicted in FIG. 4. Although the packaging 704 has been described as blister packaging and tablets, other forms of tablets, capsules, and packaging are envisioned.

The package of colors 720 generally include tablets 724 packaged in blister packaging with perforations 726 for easy measuring and making adjustments to a mixture. For example, a quarter of the color 728 can be used instead of the whole tablet 724 of a color. The packaging itself can also have perforations 730 around each tablet 724 for ease of use, and ideally, the peel-off backing 732 may reseal such that other portions 734 of a tablet 724 may be utilized at a later point in time. The package of colors 720 may include one or more colors 108 or a mix of colors 108 for a package 720, and the tablets may be half the size of the primary(ies) 104 tablets 708 as per the mixing instruction depicted in FIG. 4. The modular cosmetics kit 700 may also include a modifier 736 in a container. The container may be capable of dispensing dosages of a predetermined amount. Moreover, the modular cosmetics kit 700 may also include a mortar and pestle 740 for mixing the primary tablet 708, the color tablet 724, and/or the dispensed modifier 736. The tablets 724 and/or 708 may be of various sizes and concentrations.

In accordance with embodiments of the present disclosure, the modular cosmetic system 100 may be used to identify, eliminate, and/or reduce ingredients a consumer may be sensitive or otherwise allergic to. Moreover, simple, mineral ingredients, which can be specifically disclosed to the consumer are used such that the consumer may be able to avoid certain ingredients to achieve a same desired outcome using other ingredients. For example, mica is intentionally avoided in both pigments and the matte base. Those who experience skin irritation when wearing makeup are able to eliminate this variable (e.g., mica). Moreover, the separation of makeup media into three multifunctional parts: primaries, colors, and modifiers provides such ingredient customization. For example, modifiers tend to contain the more potentially irritating components in makeup, from oils to special-effect, synthetic ingredients such as silicones. However, the ingredients included in each modifier may be selected with the same simplistic principle as the primary and color powders for flexibility in sensitivity elimination. For sensitive skin, pigment concentration can be diluted with either primary without impacting color performance. Accordingly, synthetic ingredients, such as silicone, may not be included in a modifier. Alternatively, or in addition, an amount of synthetic ingredients, such as silicone, may be reduced when compared to conventional cosmetic products. Moreover, an amount of synthetic product, such as silicone, may be customizable based on a user's preferences. For example, a user may vary an amount and/or type of modifier based on a sensitivity to the ingredients in the modifier while still achieving a desired function and look of the cosmetic product.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The terms "determine," "calculate," "compute," and variations thereof, as used herein, are used interchangeably and include any type of methodology, process, mathematical operation or technique.

What is claimed is:

1. A modular cosmetic system comprising:
a plurality of separate and distinct primary components, wherein the plurality of separate and distinct primary components includes a first primary component in powder form and a second primary component in powder form;
a plurality of separate and distinct color components, wherein the plurality of separate and distinct color components includes a first color component in powder form and a second color component in powder form;
a plurality of separate and distinct modifier components, wherein the plurality of separate and distinct modifier components includes a first modifier component in gel form and a second modifier in liquid form,
wherein,
the plurality of separate and distinct primary components, plurality of separate and distinct color components, and the plurality of separate and distinct modifier components are mixable together to form at least one cosmetic product that can be applied to skin of a user.

2. The modular cosmetic system of claim 1, wherein the at least one cosmetic product is at least one of a foundation, a concealer, an eye shadow, an eyeliner, or a blush.

3. The modular cosmetic system of claim 2, wherein the first primary component, first color component, and first modifier component are mixable together to form a foundation cosmetic product, and the first primary component, first color component, and first modifier component are mixable together to form an eyeliner.

4. The modular cosmetic system of claim 1, wherein an adhesion quality of a first primary component is greater than an adhesion quality of a second primary component.

5. The modular cosmetic system of claim 4, wherein at least one of the first primary component and the second primary component include a translucent material composition.

6. The modular cosmetic system of claim 4, wherein a color of a first color component is different from a color of a second color component.

7. The modular cosmetic system of claim 1, wherein the at least one cosmetic product includes about two parts of at least one of a first primary component to one part of at least one of a first color component.

8. The modular cosmetic system of claim 1, wherein the at least one cosmetic product is at least one of a foundation, a concealer, an eye shadow, an eyeliner, or a blush.

9. The modular cosmetic system of claim 8, further comprising:
   a measuring device configured to measure at least one of the plurality of color components.

10. The modular cosmetic system of claim 1, wherein at least one of the plurality of primary components is a tablet including perforated portions, each perforated portion of the primary component tablet corresponding to a predetermined first measurement amount.

11. The modular cosmetic system of claim 10, wherein at least one of the plurality of primary color components is a tablet including perforated portions, each perforated portion of the color component tablet corresponding to a predetermined second measurement amount.

12. The modular cosmetic system of claim 11, wherein the predetermined first measurement amount is greater than the predetermined second measurement amount.

13. The modular cosmetic system of claim 1, wherein at least one of the plurality of separate and distinct primary components does not include mica.

* * * * *